United States Patent [19]

Broadnax, Jr.

[11] Patent Number: 5,067,950
[45] Date of Patent: Nov. 26, 1991

[54] WOUND DRAINAGE TUBE/RESERVOIR CONNECTOR

[75] Inventor: Cecil H. Broadnax, Jr., Somerset, N.J.

[73] Assignee: Johnson & Johnson Medical, Inc., Arlington, Tex.

[21] Appl. No.: 559,753

[22] Filed: Jul. 30, 1990

[51] Int. Cl.⁵ .................. A61M 1/00; A61M 25/00; A61B 19/00
[52] U.S. Cl. .................. 604/317; 604/283; 604/411; 604/905
[58] Field of Search .................. 604/88, 119, 192, 198, 604/205, 171, 283, 411, 415, 64, 905, 256, 257, 317, 318, 319, 322

[56] References Cited

U.S. PATENT DOCUMENTS

| | | | |
|---|---|---|---|
| 2,847,995 | 8/1958 | Adams | 604/198 |
| 4,161,949 | 7/1979 | Thanawalla | 128/247 |
| 4,392,499 | 7/1983 | Towse | 604/283 |
| 4,511,359 | 4/1985 | Vaillancourt | 604/411 |
| 4,564,054 | 1/1986 | Gustavsson | 141/329 |
| 4,569,674 | 2/1986 | Phillips et al. | 604/119 |
| 4,675,020 | 6/1987 | McPhee | 604/411 |
| 4,693,708 | 9/1987 | Wanderer et al. | 604/198 |
| 4,752,292 | 6/1988 | Lopez et al. | 604/283 |
| 4,768,568 | 9/1988 | Fournier et al. | 141/286 |
| 4,920,976 | 5/1990 | Calzi et al. | 128/764 |
| 4,927,423 | 5/1990 | Malmborg | 604/88 |

OTHER PUBLICATIONS

Becton–Dickinson Catalog, pp. 15–17—Vacutainer Specimen Tubes.

Primary Examiner—Ronald Frinks
Assistant Examiner—Trinh Nguyen
Attorney, Agent, or Firm—James Riesenfeld

[57] ABSTRACT

A connector that permits safe and convenient attachment of a wound drainage tube to a fluid reservoir includes a hollow penetrator whose one end is attachable to the drainage tube and whose other end is sharpened to permit it to pierce a penetrable plug that initially seals an inlet tube of the reservoir. The penetrator is covered with a stocking that initially prevents fluid from flowing out of the sharpened end. A protective skirt has one end attached to the penetrator. Its other end is open and permits the skirt to surround the inlet tube as the penetrator is moved toward the plug and then pierces the stocking and plug to permit fluid to flow from the drainage tube to the reservoir.

6 Claims, 5 Drawing Sheets

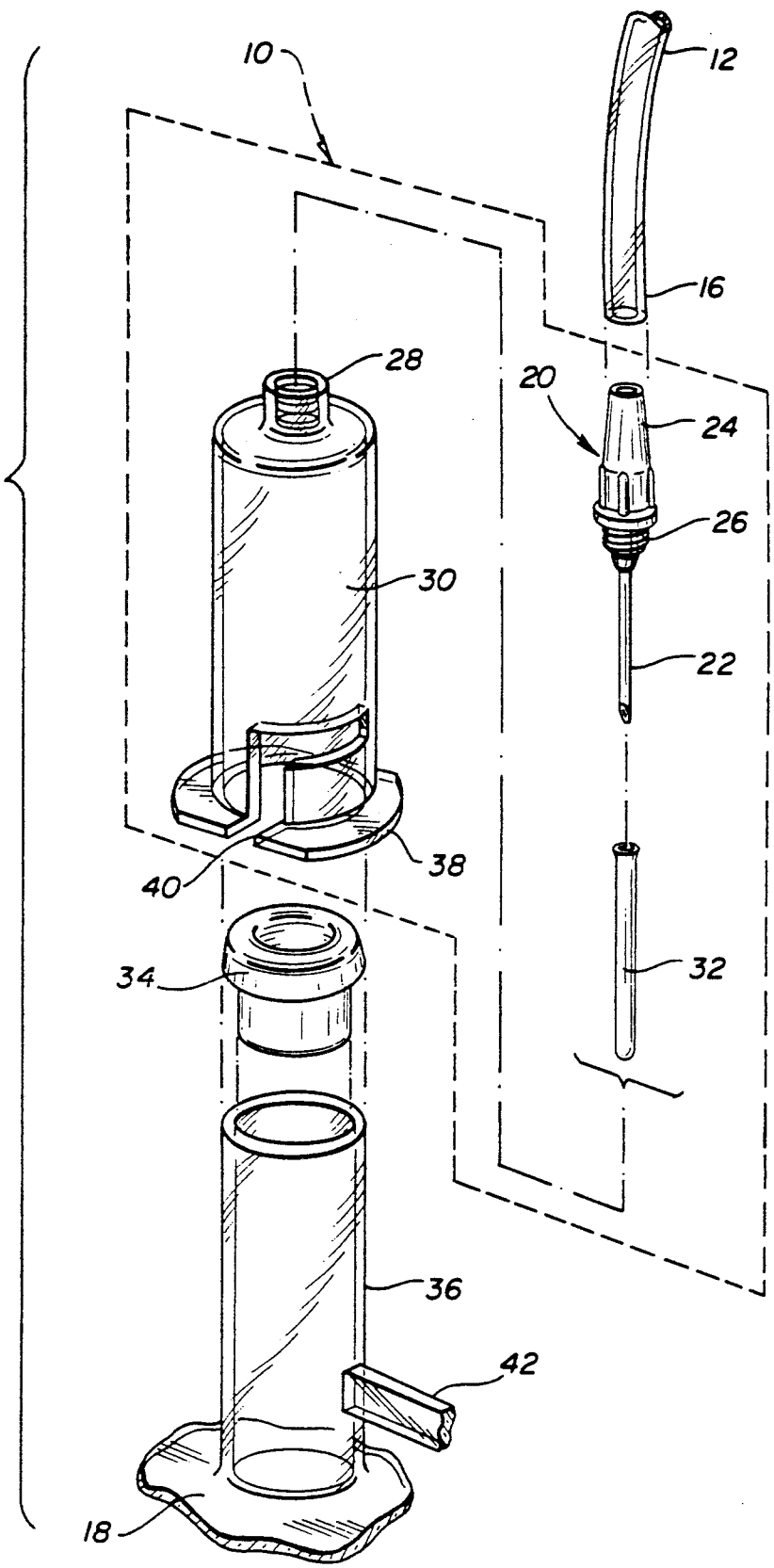

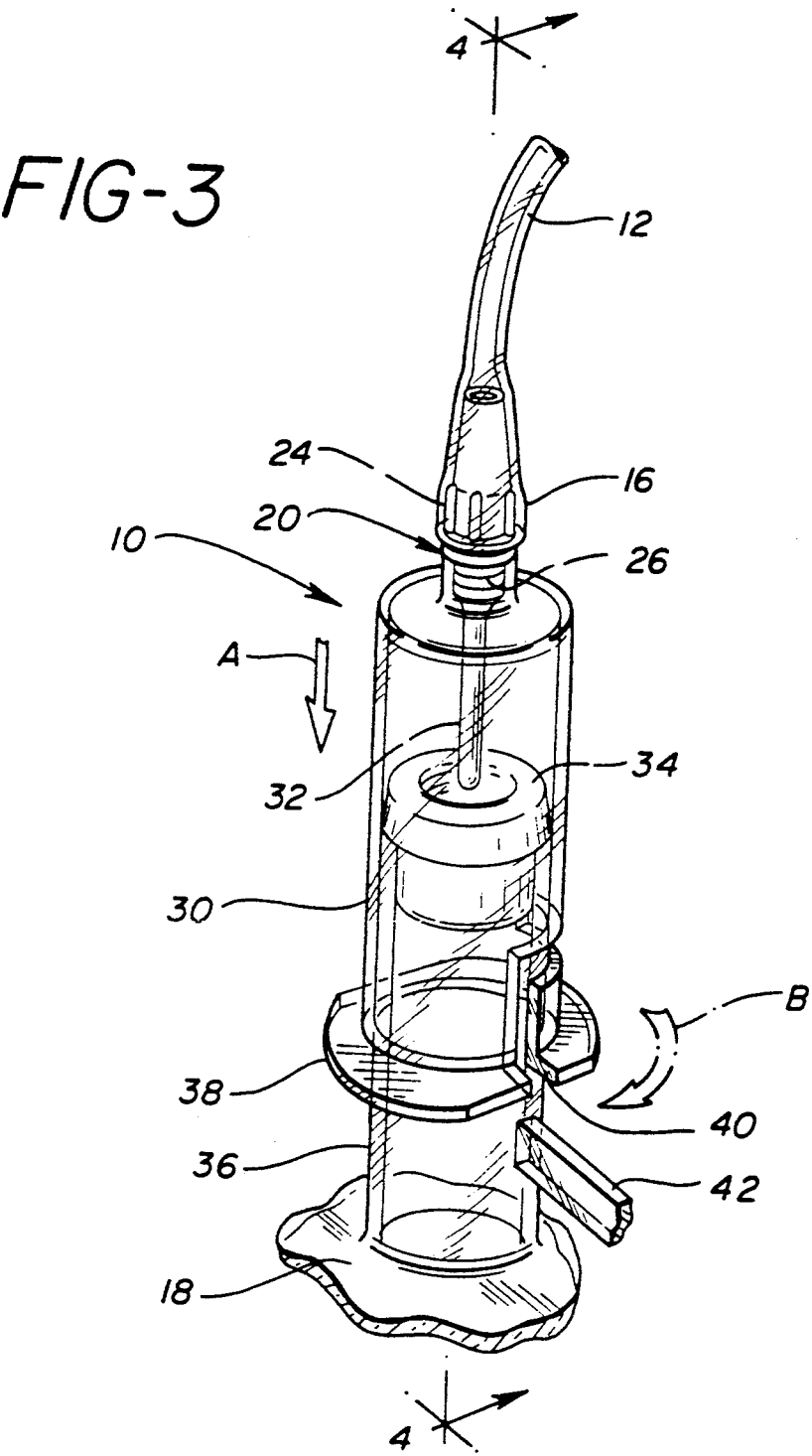

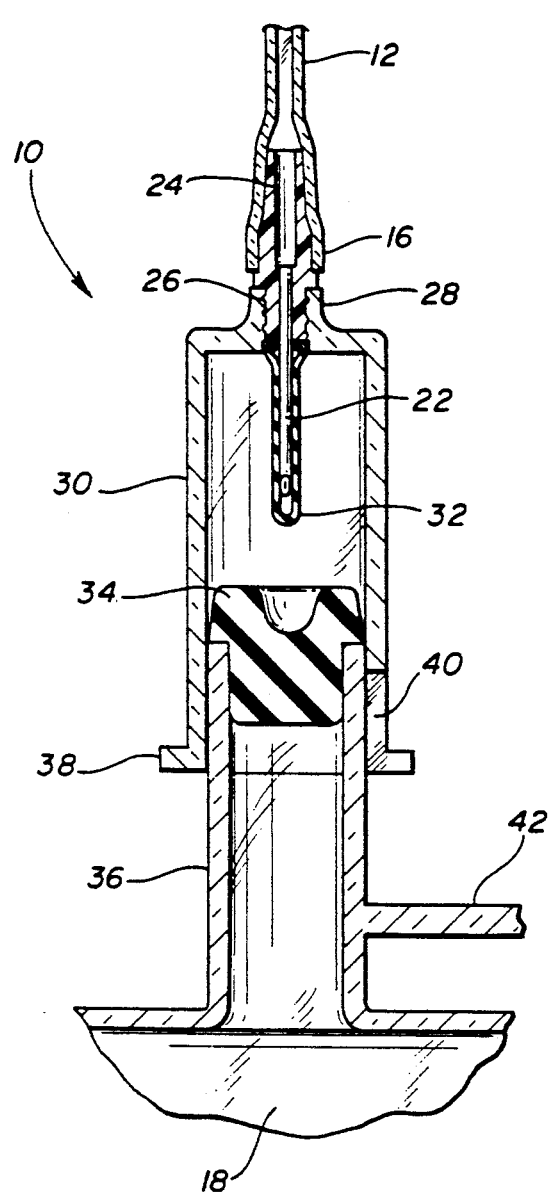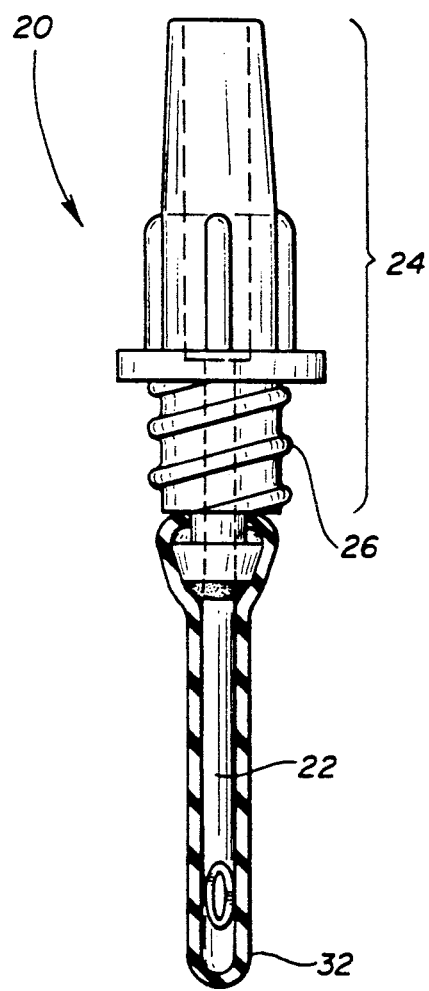

FIG-6
FIG-7
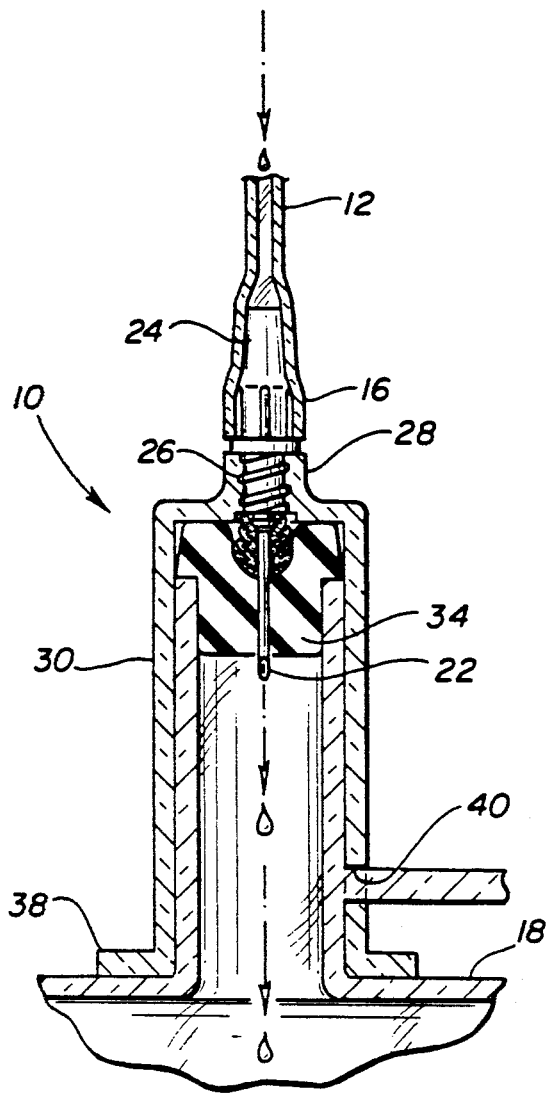
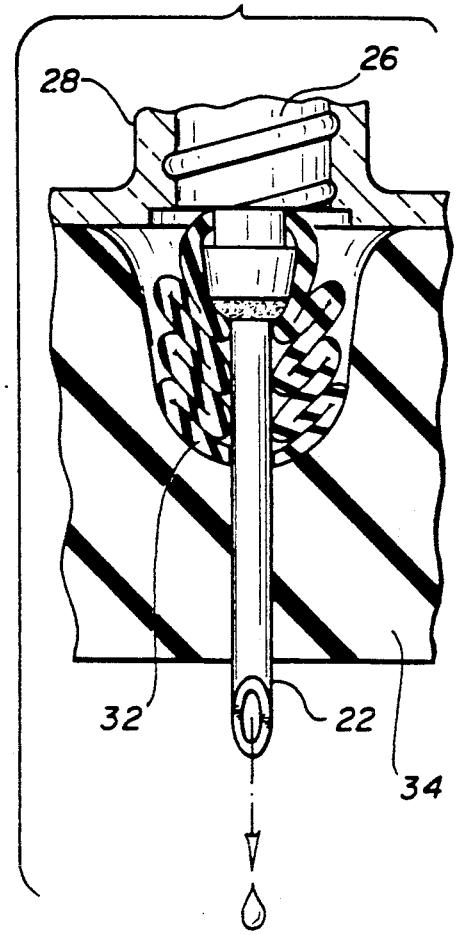
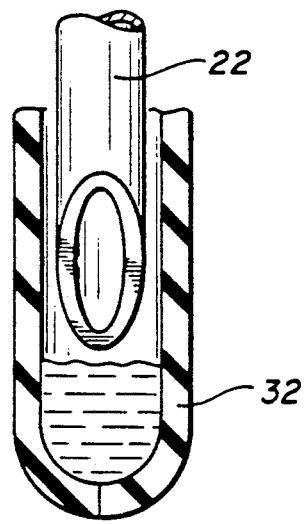
FIG-8

WOUND DRAINAGE TUBE/RESERVOIR CONNECTOR

BACKGROUND OF THE INVENTION

1. Field of the Invention

This invention relates to a connector that permits safe and convenient attachment of a wound drainage tube to a fluid reservoir.

2. Description of the Related Art

It is commonly necessary to draw various fluids from parts of a patient's body; for example, from surgical wound cavities. The procedure generally involves a flexible tube that leads out of the body from the site to be drained and that is connected to a fluid inlet on a wound drainage reservoir, which may be a vacuum drainage bottle. When the bottle is evacuated, by pumping on a second inlet for example, fluid is drawn into the reservoir. Alternatively, the reservoir may be evacuated and sealed, then stored in the evacuated state until it is used. In that case, no second inlet is needed, and fluid is drawn into the reservoir simply by attaching the drainage tube to the single inlet and opening the inlet. As the fluid enters the reservoir, the pressure in the reservoir rises. After the pressure rises above a certain level, adequate drainage is no longer achieved, and the bottle must be replaced. Of course, both the single-inlet and double-inlet bottles must be replaced when they are full. The process of removing a full bottle and replacing it with an empty one may pose a risk of contamination to the patient and/or the health care provider. There are a variety of devices that have been designed to minimize the risk in this and similar medical procedures.

U.S. Pat. No. 4,161,949, issued July 24, 1979 to Thanawalla, discloses a connector for effecting aseptic joining of two bodies to permit fluid to flow between them. The connector includes male and female elements that are telescopingly engaged to permit the fluid transfer. Both the male and female elements have a rather complex and specialized structure, requiring close tolerances.

U.S. Pat. No. 4,511,359, issued Apr. 16, 1985 to Vaillancourt, discloses a connector that is particularly adapted for continuous ambulatory peritoneal dialysis. The connector includes male and female halves in which a movable, resilient, and penetrable protector is held on the female half before attachment and retained by the male half when the female half is withdrawn. Since there is but a single protector, when the two halves are not joined together, potentially contaminating contact can be made to the unprotected assembly half (the male half before attachment; the female half after). Furthermore, close tolerances are required to assure that the friction fit of the protector in the female half is great enough to hold the protector initially but is not as great as the fit in the male half.

U.S. Pat. No. 4,564,054, issued Jan. 14, 1986 to Gustavsson, discloses a fluid transfer system that involves a puncturing member that penetrates a sealing membrane to effect the transfer. The system is designed to prevent air contamination during transfer.

U.S. Pat. No. 4,569,674, issued Feb. 11, 1986 to Phillips et al., discloses a continuous vacuum drainage system for wound drainage. The system is designed to permit a wound drainage reservoir to be removed from a vacuum pump ("base unit") without causing the partial vacuum in the reservoir to be lost thereby. Connection between the drainage tube and reservoir is made using a sleeve on the drainage tube for removable telescoping over an upstanding boss on the bottle. An O-ring seals the sleeve against the boss to prevent leakage.

U.S. Pat. No. 4,675,020, issued June 23, 1987 to McPhee, discloses a connector that uses a double-pointed hollow needle, one point of which includes a removable section. The device is designed for making connections to the interior of a sealed container, while also securely attaching to the outside of the container. Double-pointed needle devices have also been used for venous blood specimen collection, under the mark "Vacutainer" specimen tubes, by Becton-Dickinson.

U.S. Pat. No. 4,768,568, issued Sept. 6, 1988 to Fournier et al., discloses a hazardous material container and a device that permits a user to dilute the material and then fill a syringe with the diluted material without any of it escaping into the atmosphere.

U.S. Pat. No. 4,920,976, issued May 1, 1990 to Calzi et al., discloses a device for collecting and holding blood samples. The blood is held in an evacuated tube that is closed by a penetrable stopper and that has a diaphragm below the stopper, in the tube. The diaphragm forms a supplemental barrier between the interior of the tube and the environment when the stopper is removed.

U.S. Pat. No. 4,927,423, issued May 22, 1990 to Malmborg, discloses a connector for a container that has an opening which is closed by means of a pierceable closure. The connector permits a solvent to be safely introduced into a vessel containing a dry powder solute, which may be a drug.

None of the above-described related art discloses a simple connector device that broadly enables a fluid to be transferred from a tube into a reservoir, while protecting both the fluid and the operator from possible contamination from the other before, during, and after transfer.

SUMMARY OF THE INVENTION

In accordance with the present invention, a connector for joining a wound drainage tube to an inlet tube of a fluid reservoir comprises (a) a hollow penetrator, having a first end for removable attachment to the drainage tube and a second, sharpened end for penetrating the plug;

b) an initially imperforate, rupturable stocking for preventing fluid flow out of the sharpened end of the penetrator;

c) an elongated skirt for confining the sharpened end of the penetrator, having a longitudinal axis, means at a first end for removable attachment to the penetrator, and an open second end that permits the skirt to surround the inlet tube and be moved along the inlet tube in a direction parallel to the skirt axis, whereby moving the skirt along the inlet tube permits the sharpened end of the penetrator to rupture the stocking and penetrate the plug to provide a path for fluid to flow from the wound drainage tube to the fluid reservoir. The connector facilitates draining a wound into a fluid reservoir, which may be any surgical/drainage reservoir, without risking contact between the fluid and the operator.

BRIEF DESCRIPTION OF THE DRAWINGS

FIG. 2 is an exploded isometric view of a connector of the present invention.

FIG. 3 depicts a connector of the present invention being installed on the inlet tube of a reservoir.

FIG. 4 is a cross section taken along the line 4—4 of FIG. 3.

FIG. 5 is an enlarged cross section of a penetrator element of the present invention.

FIG. 6 is a cross section taken along the line 6—6 of FIG. 1.

FIG. 7 is a cross section of a penetrator of the present invention piercing an inlet tube sealing plug.

FIG. 8 is a cross section of the tip of a penetrator and stocking of the present invention.

DETAILED DESCRIPTION OF THE INVENTION

Figure 1:
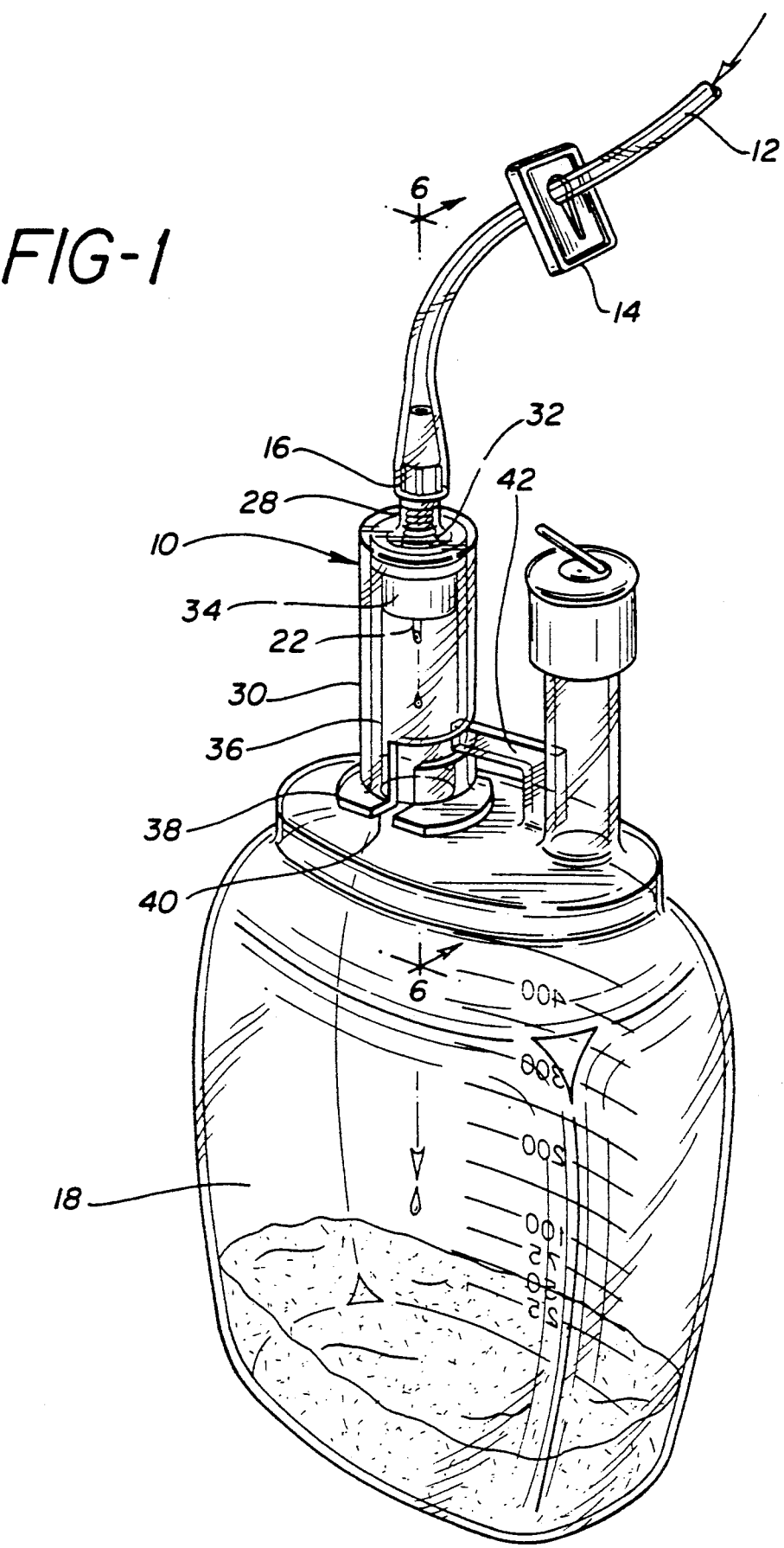
FIG. 1 depicts an isometric view of a wound drainage system using a connector of the present invention.

The present invention provides a device that permits a user to connect a wound drainage tube to a fluid reservoir with minimal risk of contact between fluid and operator. The design of the connector permits it to be adapted for broad application to any drainage tube and to any fluid reservoir that has an inlet tube.

FIG. 1 depicts an embodiment of the connector 10 of the present invention as an element of a wound drainage system. Fluid enters the proximal end of wound drainage tube 12 from a surgical wound cavity or other source (not shown). The position of slide clamp 14 determines how far the fluid travels toward the tube's distal end 16 and at what rate it flows. When slide clamp 14 and connector 10 are in the positions shown, fluid is drawn into vacuum drainage bottle (reservoir) 18.

FIG. 2 shows the elements of connector 10 in an exploded view. The distal end 16 of the drainage tube is connected to one end of penetrator 20. In a preferred embodiment, as shown, penetrator 20 comprises hollow needle 22 joined to hollow tube 24. Hollow tube 24 has exterior threads 26 over part of its length for mating with a tapped section 28 at one end of skirt 30. Alternatively, hollow tube 24 can be press fit into section 28 of skirt 30. Stocking 32 prevents fluid from flowing out of hollow needle 22 until it is ruptured by the needle. Penetrable plug 34 in inlet tube 36 seals reservoir 18 until it is penetrated by needle 22. Plug 34 could, alternatively, be a diaphragm or any other penetrable seal. Optional ledge 38, at the base of connector 10, strengthens skirt 30. Optional "L"-shaped slot 40 in skirt 30 (and in ledge 38) permits connector 10 to anchor to arm 42 on inlet tube 36. An optional anti-reflux valve (not shown) prevents fluid from accidentally flowing out of the inlet tube.

FIG. 3 shows how a connector 10 of this invention joins wound drainage tube 12 to inlet tube 36, using the optical L-shaped slot 40. The connector is first pushed along inlet tube 36 in the direction of arrow "A", causing penetrator 20 (shown in detail in FIG. 5) to rupture stocking 32 and to penetrate plug 34. Ledge 38 can provide a "stop" at the end of the "push." Connector 10 is then twisted in the direction of arrow "B" to engage arm 42. This twist attachment method protects against the connector being pulled off the inlet tube simply by applying a tension force to tube 12. Instead, removal requires that the connector first be twisted in a direction opposite to arrow B, then pulled in a direction opposite to arrow A. Note that skirt 30 extends well below the bottom of penetrator 20 to protect the user from coming into contact with the penetrator accidentally during placement or removal of the connector. Stocking 32 provides additional protection.

FIG. 4 is a cross section taken along line 4—4 of FIG. 3, which clarifies the internal structure of the connector and the attachments at each end. As shown, drainage tube end 16 surrounds the hollow tube end 24 of penetrator 20, but clearly the hollow tube end could instead be designed to surround the drainage tube end.

FIG. 5 is an enlargement of the penetrator cross section of FIG. 4, showing hollow needle 22 joined to hollow tube 24 at one end and covered with stocking 32 at its other end.

FIG. 6 is a cross section taken along line 6—6 of FIG. 1. In contrast with FIGS. 3 and 4, which depict the situation before the penetrator has pierced plug 34, FIG. 6 shows fluid passing from drainage tube 12 through connector 10 into reservoir 18. As is shown in FIGS. 6 and 7, stocking 32 does not penetrate plug 34, remaining contracted above the plug. In a preferred embodiment, stocking 32 is of an elastomeric material that returns to its original position around needle 22 as the needle is withdrawn from plug 34, sealing itself to prevent fluid from passing through (FIG. 8).

Having now described the invention, it should be readily apparent that many variations and modifications may be made without departing from the spirit and scope of the present invention.

I claim:

1. A connector for joining a wound drainage tube to a fluid reservoir that has an inlet tube sealed with an initially imperforate penetrable plug, the connector comprising
   a) a hollow penetrator, having a first end for removable attachment to the drainage tube and a second, sharpened end for penetrating the plug;
   b) an initially imperforate, rupturable stocking for preventing fluid flow out of the sharpened end of the penetrator;
   c) an elongated skirt for confining the sharpened end of the penetrator, having a longitudinal axis, means at a first end for removable attachment to the penetrator, and an open second end that permits the skirt to surround the inlet tube and be moved along the inlet tube in a direction parallel to the skirt axis, whereby moving the skirt along the inlet tube permits the sharpened end of the penetrator to rupture the stocking and penetrate the plug to provide a path for fluid to flow from the wound drainage tube to the fluid reservoir.

2. The connector of claim 1, in which the penetrator comprises a hollow needle whose first end is joined to a hollow tube having a longitudinal axis collinear with a longitudinal axis of the needle.

3. The connector of claim 2, in which the hollow tube has a threaded exterior over at least a part of its length and the means for removable attachment of the skirt to the penetrator comprises a tapped section at the first end of the skirt for receiving the threaded exterior of the penetrator.

4. The connector of claim 1, in which the stocking is self-sealing after the penetrator first ruptures the stocking and is then withdrawn from the stocking.

5. The connector of claim 1, further comprising an L-shaped slot at the second end of the skirt to permit a twist attachment of the skirt to an arm on the reservoir.

6. A wound drainage system, including
   a wound drainage tube for draining fluid from a source;

a fluid reservoir, having an inlet tube sealed with an initially imperforate penetrable plug, for collecting the fluid that flows from the source, and a connector for joining the wound drainage tube to the fluid reservoir, the connector comprising a) a hollow penetrator, having a first end for removable attachment to the drainage tube and a second, sharpened end for penetrating the plug;

b) an initially imperforate, rupturable stocking for preventing fluid flow out of the sharpened end of the penetrator;

c) an elongated skirt for confining the sharpened end of the penetrator, having a longitudinal axis, means at a first end for removable attachment to the penetrator, and an open second end that permits the skirt to surround the inlet tube and be moved along the inlet tube in a direction parallel to the skirt axis.

* * * * *